United States Patent [19]
Baer et al.

[11] Patent Number: 5,283,037
[45] Date of Patent: * Feb. 1, 1994

[54] CHEMICAL SENSOR UTILIZING A SURFACE TRANSVERSE WAVE DEVICE

[75] Inventors: Richard L. Baer; Curt Flory, both of Los Altos, Calif.

[73] Assignee: Hewlett-Packard Company, Palo Alto, Calif.

[*] Notice: The portion of the term of this patent subsequent to Jul. 14, 2009 has been disclaimed.

[21] Appl. No.: 792,975

[22] Filed: Nov. 15, 1991

Related U.S. Application Data

[63] Continuation-in-part of Ser. No. 251,149, Sep. 29, 1988, Pat. No. 5,130,257.

[51] Int. Cl.$^5$ ............... G01N 33/00; G01N 27/00; H01L 41/00; H01L 41/08
[52] U.S. Cl. ............... 422/82.01; 310/311; 310/312; 310/313 D; 73/61.45; 73/61.49; 422/68.1; 436/149; 436/151
[58] Field of Search ............... 310/311, 312, 313 D, 310/313 R; 422/68.1, 82.01; 436/149, 151; 73/61.45, 61.49

[56] References Cited

U.S. PATENT DOCUMENTS

| | | | |
|---|---|---|---|
| 4,025,954 | 5/1977 | Bert | 358/213 |
| 4,312,228 | 1/1982 | Wohltjer | 73/597 |
| 4,735,906 | 4/1988 | Bastiaans | 436/327 |
| 4,767,719 | 8/1988 | Finlan | 436/501 |
| 4,789,804 | 12/1988 | Karube | 310/311 |
| 4,847,193 | 7/1989 | Richards | 435/6 |
| 4,965,479 | 10/1990 | Elliott et al. | 310/313 D |

FOREIGN PATENT DOCUMENTS 0246846 5/1987 European Pat. Off. ... G01N 33/543

OTHER PUBLICATIONS

Showko Shiokawa et al, Design of SAW Sensor in Liquid, Japanese Journal of Applied Physics, vol. 27, (1988) Supp. 27-1, pp. 142-144.

Hank Wohltjen, Surface Acoustic Wave Microsensors, Transducers 1987.

Shiokawa, S. & Moriizumi, "Design of SAW Sensor in Liquid", Proceedings of the 8th Symposium on Ultrasonic Electronics/Dec. 8-10, 1988, Mar. 27, 1988, Suppl. 27-1, Tokyo, Japan; pp. 142-144.

T. Moriizumi, et al. "New sensor in Liquid Using Leaky Saw", 1987 Ultrasonics Symposium pp. 579-582, Oct. 14-16, 1987.

Thompson et al. Ultrason SYMP Proc., (1), 261-266, 1986, in Chemical Abstract (22) 210466k.

Primary Examiner—James C. Housel
Assistant Examiner—Milton I. Cano

[57] ABSTRACT

A sensor suitable for use as a viscosity sensor, a chemically selective sensor, or a chemically specific sensor. The sensor is a surface transverse wave (STW) or Love Wave device that, for solute concentration measurements, includes a chemically reactive layer selected to react with the solute to be measured. The surface trapping structure in this device can include dielectric material either as a protective coating or as the core material of the surface trapping structure. The substrate material and cut are selected so that only shear horizontal acoustic waves are produced. Nonpiezoelectric portions of this device can be utilized in the region in which chemicals react the sensor and/or in the region in which energy is converted between electrical and acoustical forms.

17 Claims, 8 Drawing Sheets

CHEMICAL SENSOR UTILIZING A SURFACE TRANSVERSE WAVE DEVICE

This application is a continuation-in-part of U.S. patent application Ser. No. 07/251,149 filed Sep. 29, 1988, now U.S. Pat. No. 5,130,257.

FIELD OF THE INVENTION

This invention relates in general to mass sensors and relates more particularly to a chemical sensor utilizing a surface transverse wave device or a Love Wave device. In the following, the first digit of a reference numeral indicates the first figure in which is presented the element referenced by that reference numeral.

BACKGROUND OF THE INVENTION

Piezoelectric resonators have been used as microgravimetric immunoassay devices (See, for example, Joy E. Roederer and Glenn J. Bastiaans, "Microgravimetric Immunoassay with Piezoelectric Crystals", Anal. Chem. 1983, 2333-2336). Changes in the amount of mass attached to the surface cause shifts in the resonant frequency. A device that has an output signal that is significantly affected by the amount of mass attached to one of its surfaces will be referred to herein as a "mass sensor". Selective mass detection is achieved by coating the surface of the piezoelectric crystal with a chemically reactive layer that preferentially reacts with the substance to be detected such that the mass of the chemically reactive layer changes. Such devices function as chemical sensors that can measure the concentration of the selected class of compounds in a solution into which this sensor is immersed. For example, to measure the concentration of specific antibodies in a solution, a sensor is utilized in which the chemically reactive layer contains the antigen(s) corresponding to these antibodies. The concentration of the antibodies in a liquid can be measured by immersing the sensor in the liquid and inferring the change in mass from the change in resonant frequency of the sensor.

The mass sensitivity (i.e., the fractional frequency change divided by the mass change of material deposited on the surface of the sensor) increases as the mass of a bulk wave resonator is decreased or, correspondingly, as the resonator thickness is decreased. A practical lower limit of about 100 microns, corresponding to a resonance frequency of about 20 MHz, is imposed on resonator thickness by manufacturing difficulties. Consequently the sensitivity of a bulk wave resonator sensor is limited.

Surface acoustic wave (SAW) devices have also been used as mass sensors. Mass attached to the surface of the waveguide affects the velocity of wave propagation along the waveguide, thereby producing a phase shift in the output signal from the waveguide. The effective mass per unit length of the waveguide is determined by the penetration depth of the wave in the substrate. In the case of a SAW device, this penetration depth is about one wavelength. As the frequency is increased, the wavelength is decreased and the sensitivity goes up. The concentration of the antigen can be determined from this phase shift.

Bulk wave resonators and waveguides are not particularly sensitive mass sensors because their mass per unit length is relatively large. Surface Acoustic Wave (SAW) devices also make poor chemical sensors in applications which require the immersion of the sensor in a liquid, because the dominant acoustic displacement component couples strongly to compressional waves in the liquid. The reason for this is as follows. The dominant shear vertical component of SAW motion is normal to the surface so that acoustic waves in a SAW device couple to acoustic waves in the liquid. Since the acoustic propagation velocities of Rayleigh waves in solids are almost universally higher than the velocities of compressional waves in liquids, there always exists a direction of radiated acoustic waves in the liquid that, at the surface of the waveguide, are in phase with the Rayleigh mode of the SAW device. Consequently energy will radiate away from the SAW device into the liquid, causing an unacceptable amount of insertion loss.

Lamb Wave devices also make poor chemical sensors for a related reason (See, for example, R. M. White, P. J. Wicher, S. M. Wenzel, and E. T. Zellers, "Plate Mode Ultrasonic Oscillator Sensors", IEEE Trans., vol. UFFC-34, #2, pp. 163.). Lamb wave devices have the same dominant acoustic particle velocity component as SAW devices—i.e., it is also a dominant Shear Vertical wave device and therefore acoustic waves in a Lamb device will couple into acoustic waves in a liquid in which the Lamb Wave device is immersed. However, by decreasing the thickness of the waveguide, the velocity of the mode can be caused to fall below that of the surrounding liquid. This prevents phase matching and hence prevents the radiation of energy into the liquid. Unfortunately, this decreased thickness also causes the velocity of the Lamb Wave to be a strong function of the density of the liquid. This effect masks the mass sensitivity of the sensor. In addition, such a thin waveguide is fragile and is therefore easily damaged.

SUMMARY OF THE INVENTION

In accordance with the disclosed method of testing, a Surface Transverse Wave (STW) device or a Love Wave device is immersed in a liquid under test, a signal is applied to such device and the velocity of acoustic wave propagation in the crystal is measured. This measurement can be made, for example, by observing the phase or frequency of an output signal from the STW or Love Wave device. When this device is coated with a chemically reactive layer that reacts selectively with a preselected component of a liquid within which it is immersed in such a manner that the mass of this layer changes, then this method measures the concentration of such solute in the liquid solution. Such reaction can take the form of binding this component to the chemically reactive layer, thereby increasing the mass of this layer. Such reaction can alternatively take the form of removing a portion of this layer, thereby decreasing the mass of this layer. Such change in mass will change the acoustic velocity of this acoustic mass sensor. When this device has no such chemically reactive layer, it measures the viscosity of the liquid. Such an STW or Love Wave device, having no chemically reactive layer, is also used to subtract such viscosity component from the output signal of an associated STW or Love Wave device having a chemically reactive layer.

In accordance with the illustrated preferred embodiment, this sensor consists of a Surface Transverse Wave (STW) device or a Love Wave device having a chemically reactive layer to attach a preselected class of compounds that are to be measured. An STW or Love Wave device is utilized as a mass sensor, because it exhibits a much better performance than the prior art Bulk Wave, Lamb Wave and Surface Acoustic Wave (SAW) devices discussed in the Background of the Invention. Depending on the velocity of the acoustic wave, the coupling of the Shear Vertical acoustic wave in SAW and Lamb Wave devices to wave motion in the liquid leads to high attenuation for the case of SAW devices and to high sensitivity to changes in liquid density in the case of Lamb Wave devices. The present mass sensors therefore overcome these limitations of these other types of acoustic wave sensors.

This sensor can take the form of a delay line in which an input signal is applied to an input transducer to produce an acoustic wave that travels to an output transducer at which an output signal is produced. The delay between application of the input signal and detection of the output signal is a function of the amount of mass attached to a "sensing surface" of this delay line, thereby enabling the amount of attached mass to be determined.

This sensor can also take the form of a resonator in which the resonant frequency is a function of the amount of mass bound to the sensing surface of the mass sensor. In a 1-port embodiment, a single interdigital transducer (IDT) is surrounded by two reflective gratings. The grating and IDT characteristics and the spacing between the gratings determines the resonance frequency. The amount of mass attached to the sensing surface of the sensor can be determined from the change in resonant frequency of this resonator. Any circuit that measures the change in velocity of the acoustic waves caused by attachment of material to the sensing surface will function to adapt the STW device or Love Wave device into a mass sensor.

The IDTs and grating and/or plate are formed on the surface of the substrate using conventional integrated circuit fabrication processes, such as film deposition and etching. The mass loading and electrical shorting produced by the addition of the grating and/or plate traps the wave and prevents excess attenuation. The grating provides stronger trapping than the plate, for equivalent thicknesses and densities. Waves that are more strongly trapped have shallower penetration depths, thereby producing greater electrical coupling and mass sensitivity.

The STW device and Love Wave device each includes: at least one transducer for converting between electrical and acoustic signals; a surface trapping structure for trapping these acoustic signals at the sensing surface of the device; and a chemically reactive layer to react with selected chemicals to be detected. When the chemically reactive layer is selective for a narrow class of compounds, this sensor functions as a chemical sensor that measures the concentration of this narrow class of compounds.

The Love Wave sensor and the STW sensor differ in that the Love Wave sensor utilizes a plate as the trapping structure and the STW sensor utilizes a grating as the trapping structure. Because the surface trapping structure traps the wave energy within a narrow region adjacent to the chemicals bound to this acoustic wave device, this device functions as a mass sensor having a sensitivity on the order of $10^7$, $10^3$ and $10^2$ times the sensitivity of the Bulk Wave, SAW, and Lamb Wave devices, respectively, discussed in the Background of the Invention. Such trapping reduces the effective mass of the waveguide region so that the amount of mass attached to the chemically reactive layer represents an increased fractional change in the total mass of the waveguide region, thereby increasing the sensitivity of the sensor.

The grating and plate each adds mass to the surface, thereby producing a local slowing of the acoustic wave which traps this wave near the surface. There are two other ways in which the grating or plate can slow the acoustic waves at the surface. If the plate or grating is conductive, it can short out the electric field at the surface of the substrate, thereby reducing the piezoelectric component of the stiffness of the piezoelectric crystal at the surface. Because the wave velocity is proportional to the square root of the crystal stiffness, this reduces the wave velocity at the surface. Also, for a grating-type surface trapping structure, the discontinuities present at the edges of the grating elements produce reflections that reduce wave velocity.

It is generally advantageous for the surface trapping structure to be metallic, because metals typically have a high density and because metals are conductive, thereby producing an increased amount of wave velocity slowing by shorting out, at the surface of the substrate, the piezoelectric component of the substrate stiffness. However, the surface trapping structure can also be formed out of a dielectric material or a combination of dielectric and conductive materials. Although the lower density of such material means that it will have to be thicker than a corresponding metallic surface trapping structure, for devices in which a dielectric layer is required for other purposes, the dielectric surface trapping structure can be formed as part of that process step, thereby avoiding the need for a separate step to produce a metallic surface trapping structure. Also, such a nonmetallic surface trapping structure is not subject to the corrosion that can occur in many liquid environments if this trapping structure is metallic. For sensors to be used in such environments, the use of a dielectric trapping structure avoids the need for separate steps to produce the trapping structure and to produce a corrosion resistant layer over this trapping structure, as would be required if this structure were metallic.

The penetration depth of acoustic waves into Love Wave devices and STW devices ranges from a fraction of an acoustic wavelength to a few acoustic wavelengths, depending on the characteristics of the device and the type of wave motion. Because acoustic waveguide devices can be easily fabricated at frequencies of up to several gigahertz using standard photolithographic techniques, the penetration depths can be reduced to several microns. When the acoustic wave is generated by an interdigital transducer (IDT), the minimum wavelength is equal to four times the minimum linewidth that can be fabricated, which presently is on the order of a half micron. The frequency of the electrical oscillator that is coupled to the input transducer is equal to $v/\lambda$, where $v$ is the velocity of the acoustic wave in the acoustic device and $\lambda$ is the wavelength of the acoustic wave. Thus, for STW devices utilizing minimum linewidth IDTs, the frequency of the oscillator is on the order of 2.5 GHz.

The substrate is preferably piezoelectric so that a pair of interdigital transducers can be utilized to convert an input electrical signal to an acoustic signal that travels from the first transducer to the second transducer to produce an output signal. It is particularly advantageous to utilize a piezoelectric substrate that is cut such that the transducers couple energy efficiently into Shear Horizontal acoustical waves in the substrate. Because the wavelength of the acoustic wave is determined by the spacing between the fingers of the IDT and because the velocities of the longitudinal, shear vertical and shear horizontal acoustic waves are generally unequal, the IDT is driven by an electrical signal of frequency selected to couple energy substantially only into the shear horizontal mode.

Certain crystal orientations of the piezoelectric substrate are particularly advantageous for this mass sensor. Because the vertical component of acoustic vibration radiates wave energy into a surrounding liquid, it is advantageous for the choice of material, crystal cut and frequency to be such that this vertical component is substantially eliminated. Typical piezoelectric crystals utilized as the substrate include quartz, $LiNbO_3$ and $LiTaO_3$.

Quartz is a particularly good choice for several reasons. The variation of acoustic propagation velocity with temperature is relatively small in quartz. Quartz is also a particularly good choice because there are certain crystal cuts of quartz for which the shear horizontal wave, which is used in the sensor, is completely decoupled from the Rayleigh-like wave. This is advantageous because the Rayleigh-like wave radiates energy into an enclosing liquid medium, thereby reducing device sensitivity as a mass sensor. In addition, because quartz capillaries are utilized in a wide number of chemical separation processes, such as electrophoresis, there is a large volume of literature regarding chemically reactive layer materials that are suitable for application to a top surface of this mass sensor to make this sensor specific for the chemicals bound by that chemically reactive layer. This is important in embodiments for which there is no protective layer between the substrate and the chemically reactive layer.

The quartz crystal is a member of the trigonal 32 crystal class. Crystals of this class support pure shear horizontal waves for propagation in the crystal Y-Z plane, with polarization (i.e., acoustic particle displacement) along the crystal X axis. Therefore, pure shear horizontal waves can be launched along the surface for any crystal cut in which the crystal X Axis lies in the plane of the surface. These cuts are sometimes referred to as Y-rotated Z-cuts, since they correspond to cuts in which the surface normal is a vector in the Y-Z plane. The cut can be defined by the rotation of the surface normal about the X axis in the direction of the Y axis. This class of cuts includes the ST cut which corresponds to a rotation angle of 38.4°. Another advantageous cut is a 36° rotation of the surface normal toward Y from the Z axis. This cut is advantageous because it exhibits a reduced temperature sensitivity. In general, substantial temperature insensitivity is achieved if this rotation is within the range from 35°-37°.

In some alternate embodiments, an input transducer launches acoustic waves in a first piezoelectric region. These waves are then coupled through a nonpiezoelectric region to a second piezoelectric region in which the acoustic wave is converted back into an electrical signal. This nonpiezoelectric region is coated with a chemically reactive layer and is in contact with the liquid to be tested. In other embodiments, the second piezoelectric region is replace by a grating that reflects the wave back to the input transducer, thereby producing a resonant cavity type of sensor. This type of sensor has the advantage that the portion of the sensor in contact with the liquid can be of a less expensive material than typical piezoelectric materials, thereby enabling the manufacture of devices in which this portion of the sensor is an inexpensive disposable component.

The reasons for the improved sensitivity of STW devices and Lamb Wave devices as mass sensors can be seen from the following analysis of the various types of acoustic wave devices. Acoustic mass sensors can be broadly classified by the waveguiding structure utilized for any particular implementation. These broad classes are Bulk Wave, Plate Wave and Surface Wave devices. These acoustic sensors can be subclassified by the orientation of the acoustic wave motion with regard to the sensing surface in contact with the chemical(s) to be sensed. These types of wave motion are: (i) Longitudinal Wave motion in which material displacement is in a direction parallel to the direction of propagation of the wave; (ii) Shear Vertical Wave motion in which material displacement is in a direction perpendicular to both the sensing surface and the direction of wave propagation; and (iii) Shear Horizontal wave motion in which material displacement is perpendicular to the direction of propagation and parallel to the sensing surface. The terms "horizontal" and "vertical" are defined in relation to the sensing surface which is parallel to both the direction of propagation and the direction of horizontally polarized particle displacement.

All acoustic sensors are in one of these nine subclasses. Each of these nine subclasses can be further subdivided according to the details of the waveguiding structure. Waveguiding is utilized to prevent losses of acoustic energy due to diffraction of the acoustic wave. In a Bulk Wave device, no waveguiding structure is provided. Typically, the wavefront is so wide that diffraction losses are not significant. In a Plate Wave device, the acoustic energy is confined in one dimension by the top and bottom surfaces of a plate. This concept can be extended to structures like rods in order to provide guiding in two dimensions. The guiding surfaces confine the acoustic wave through internal reflection. In a Surface Wave device, the acoustic energy is confined in the vertical direction (i.e., the direction of the normal to the sensing surface) in a region adjacent to the sensing surface. Such confinement can occur because of the presence of a guiding layer at the surface or because of the nature of the boundary conditions at the sensing surface. It is difficult to realize sensors that fall into certain classes, such as Surface Wave sensors with Longitudinal Wave motion, because of the physics of the acoustic boundary conditions. In the case of sensing in liquids, sensors in some of these classes are more advantageous than other classes.

The mass sensitivity of a sensor varies inversely as the square root of the mass per unit surface area of the acoustic waveguide. Therefore, the most sensitive mass sensors are: (i) Surface Wave sensors in which the acoustic wave has a low penetration depth away from the sensing surface; and (ii) Plate Wave sensors utilizing an exceedingly thin plate.

The coupling of energy from the acoustic waves in the sensor into acoustic waves in the liquid into which the sensing surface is immersed also affects the sensitivity of the sensor. Since liquids support shear waves only through the very weak viscous forces, shear waves cannot be significantly excited in a liquid. However, when an acoustic wave having a shear vertical component is excited in the sensor adjacent to the sensing surface, longitudinal waves are excited in the liquid adjacent to the sensing surface.

If the acoustic wave in the sensor travels along the sensing surface with a velocity that is higher than the speed of sound in the liquid, then there will be a direction of propagation within the liquid at which the phase fronts of the acoustic wave in the liquid will travel in synchronism with those of the surface acoustic wave, thereby radiating energy away from the acoustic wave in the sensor. Therefore, if this wave has a shear vertical component, then the resulting radiation of energy into the liquid will attenuate this acoustic wave, thereby reducing sensitivity.

If the acoustic wave in the sensor travels along the sensing surface with a velocity that is lower than the speed of sound in the liquid, then much of the acoustic energy of the wave travels in the liquid, making this sensor sensitive to liquid parameters, such as density. Therefore, a mass sensor of highest sensitivity utilizes guided Shear Horizontal waves, because such waves do not extend significantly into the liquid and do not significantly radiate energy into the liquid. This class consists of Love Wave and STW sensors. As will now be shown, all of the other classes of acoustic sensors have problems that limit their sensitivity to levels much lower than for the Love Wave and STW sensors.

The Quartz Crystal Microbalance (QCM) is a Bulk Wave sensor that utilizes shear horizontal waves. Manufacturing considerations mandate that the crystal be relatively thick. Because the sensitivity varies inversely as the square root of the mass of the wave guiding region, such a thick waveguiding region produces a much lower sensitivity than that produced by surface wave sensors.

Surface Acoustic Wave (SAW) sensors, also known as Rayleigh Wave sensors), utilize waves that are predominantly Shear Vertical. The energy losses associated with this wave motion causes high attenuation. In order to moderate this attenuation, low frequencies and short path lengths must be used. This limits the sensitivity to values much lower than those available from other surface wave sensors.

Lamb Wave sensors and Flexural Plate Wave (FPW) sensors utilize Shear Vertical and/or Longitudinal wave motion. In general, the Lamb Wave sensor is insensitive because manufacturing considerations dictate that the plate be relatively thick, thereby decreasing its sensitivity. The FPW sensor is the limiting case of a Lamb Wave sensor for small plate thickness. Small plate thicknesses are achieved by using silicon IC manufacturing techniques to etch a region to a small enough thickness to support the flexural plate mode in that region. The flexural plate mode has the advantage, compared to the lamb Wave sensor, of exhibiting an acoustic velocity less than the acoustic velocity of most liquids, thereby avoiding radiating acoustic energy into the liquid. However, the FPW sensor is sensitive to small changes in liquid density, pressure and temperature because this wave extends into the liquid. It is also a relatively fragile device because of the thinness of the plate in the region carrying the flexural plate mode acoustic wave.

Acoustic Plate Mode (APM) sensors utilize Shear Horizontal wave motion. Manufacturing considerations dictate that the plate be relatively thick so that this device has a much lower sensitivity than surface wave devices. Silicon IC fabrication techniques are not applicable in this case because the piezoelectric films that are used in the FPW device cannot readily be used to generate Shear Horizontal waves.

Surface Skimming Bulk Wave (SSBW) sensors utilize Shear Horizontal wave motion. This device differs from SAW devices by the orientation of the crystal, direction of propagation and frequency of operation. This wave receives no guiding from the surface boundary conditions. Consequently, the wave diffracts into the bulk of the material, causing a high level of attenuation. This diffraction also decreases the sensitivity of the sensor because a significant portion of the received signal at the output transducer has traveled below the surface and therefore has not sensed surface changes.

Love Wave sensors also utilize Shear Horizontal wave motion. These sensors differ from SSBW sensors by the inclusion of a plate that functions as a surface trapping structure to trap the acoustic wave at the surface of the sensor. Because the acoustic wave is trapped in a narrow waveguiding region adjacent to the sensing surface, this sensor is very sensitive to changes in surface mass. Because this device utilizes a Shear Horizontal acoustic wave that does not radiate or extend significantly into the liquid, it is insensitive to changes in the liquid density, pressure and temperature and is much more sensitive than SSBW sensors.

Surface Transverse Wave (STW) sensors also utilize Shear Horizontal wave motion. This sensor differs from the Love Wave sensors only by the replacement of the surface trapping plate with a surface trapping grating. This grating provides stronger surface trapping than the plate utilized in a Love Wave sensor, so that this sensor is even more sensitive than the Love Wave sensor. Love Wave sensors and STW sensors are both much more sensitive than the other acoustic sensors.

Because the coupling to longitudinal acoustic modes in the liquid has been eliminated, this sensor is sensitive enough to measure the viscosity of the liquid. To enable this STW device to serve as a chemical sensor, on top of the top surface of the STW device is applied an additional layer that selectively reacts with a chemical class of interest. When such a sensor is immersed in a liquid containing chemicals in this class, such chemicals react with the surface of the sensor, thereby changing the mass loading of this top surface. For example, antibodies can be bound to the top surface of the sensor, whereby this sensor is chemically specific for the corresponding antigens. Conversely, the antigen can be bound to the top surface so that this sensor is chemically specific for the corresponding antibodies. Many other pairings of materials that selectively react with one another are well known, for example, from chemical separation processes, such as electrophoresis. Similarly, the chemically reactive surface can dissolve in the liquid component to be measured. In such an embodiment, the mass of the chemically reactive surface will decrease as a result of immersion in this liquid.

DESCRIPTION OF THE PREFERRED EMBODIMENT

Figure 1:
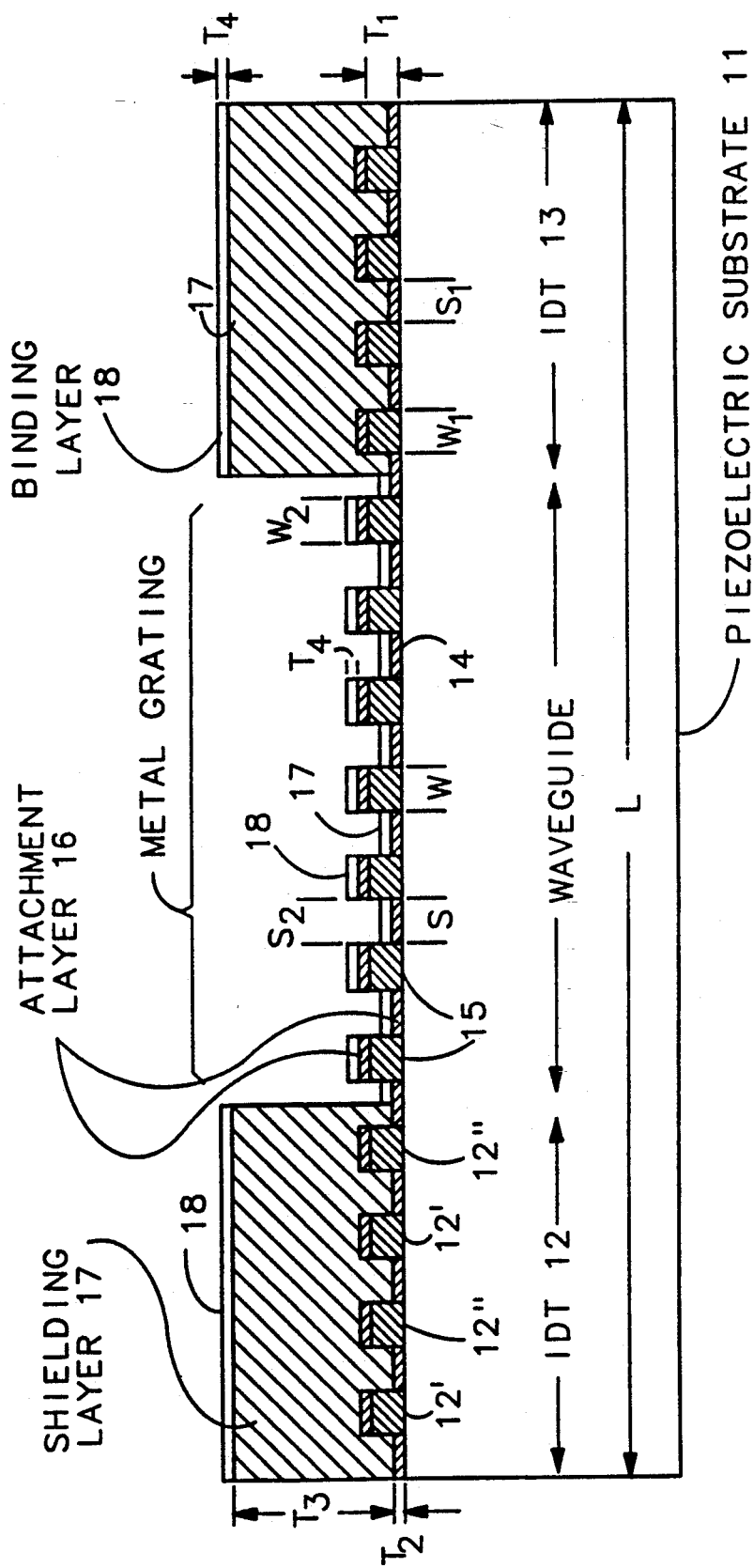
FIG. 1 is a side cross section of a surface transverse wave (STW) waveguide sensor that is suitable for use as a viscosity sensor and/or a chemical sensor.
Figure 4:
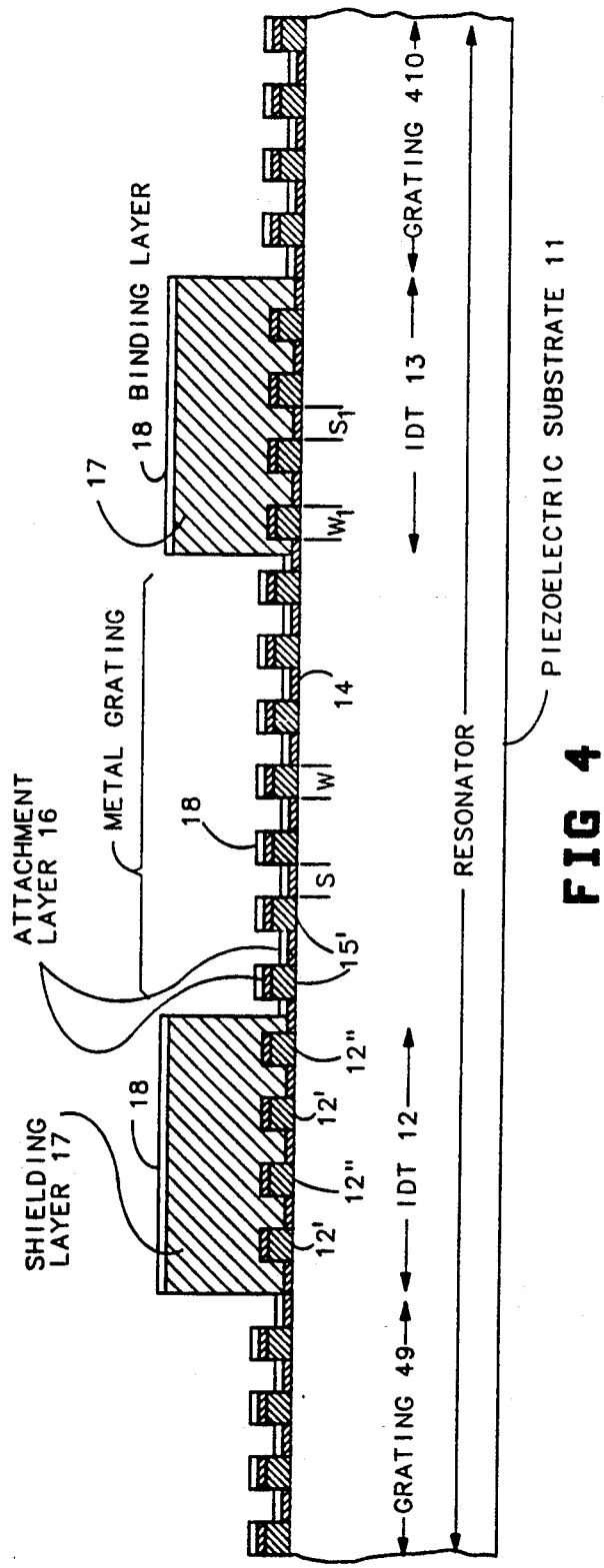
FIG. 4 is a side cross section of a surface transverse wave 2-port resonator sensor that is suitable for use as a viscosity sensor and/or a chemical sensor.

In FIG. 1, on a piezoelectric substrate 11, such as quartz, $LiTaO_3$ or lithium niobate ($LiNbO_3$), are formed an input transducer, such as interdigital transducer (IDT) 12 having electrodes 12' and 12", and an output transducer, such as interdigital transducer (IDT) 13. These IDTs have a typical thickness $T_1$ on the order of 0.1-1.0 micron, a width $W_1$ on the order of 1-100 microns and a spacing $S_1$ on the order of 1-100 microns. Reflective gratings 49 and 410 in FIG. 4 are optionally placed at the outside edge of each IDT in order to form a 2-port resonator. These transducers and gratings can be formed by well known photolithographic techniques. Typical dimensions for this device are: 10 mm long and 3 mm wide, on a 0.5 mm thick substrate.

In this embodiment, the substrate is piezoelectric and is cut to couple energy from IDT 12 substantially only into shear horizontal waves in substrate 11. The choices of substrate material and cut are also made to enable trapping of surface transverse waves at a surface (referred to herein as the "sensing surface") of the substrate at which these waves are to be trapped by a surface trapping structure. The substrate should also: (1) exhibit low acoustic loss (i.e., have low viscous attenuation); (2) have a high dielectric constant and high electromechanical coupling constant to minimize the parasitic electrical effects of liquid loading upon the transducer; and (3) have a low variation of velocity with temperature. Quartz has the advantage of exhibiting a low temperature variation of the acoustic velocity. Lithium Niobate has the advantage of better piezoelectric coupling to IDTs 12 and 13. The ST-cut of Quartz (typically used for SAW devices) can be used for STW devices by rotating the propagation direction 90 degrees (See, for example, D. F. Thompson and B. A. Auld, "Surface Transverse Wave Propagation Under Metal Strip Gratings", 1986 Ultrasonics Symp. Proc., IEEE Cat. #86CH2375-4, pp. 261.).

In general, any Y-rotated Z-cut of quartz can be utilized because these cuts produce an acoustic device in which the shear horizontal wave and the shear vertical wave are decoupled. This enables pure surface transverse waves to be generated by the IDTs and avoids producing shear vertical waves which can radiate energy into any encapsulating liquid medium. The ST cut, arises for a rotation angle of 38.4° of the surface normal from the Y axis toward the Z axis. Another particularly useful cut occurs when this rotation angle is 36 degrees, because this cut produces a particularly low temperature sensitivity of the resulting STW device.

Figure 2:
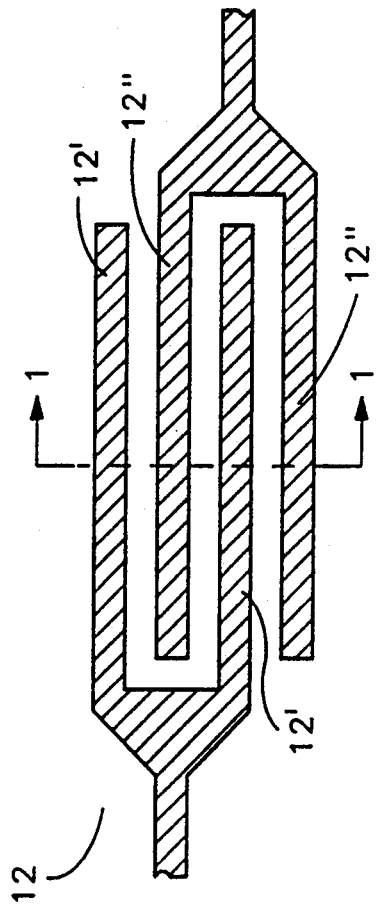
FIG. 2 is a top view of a typical IDT.
Figure 3:
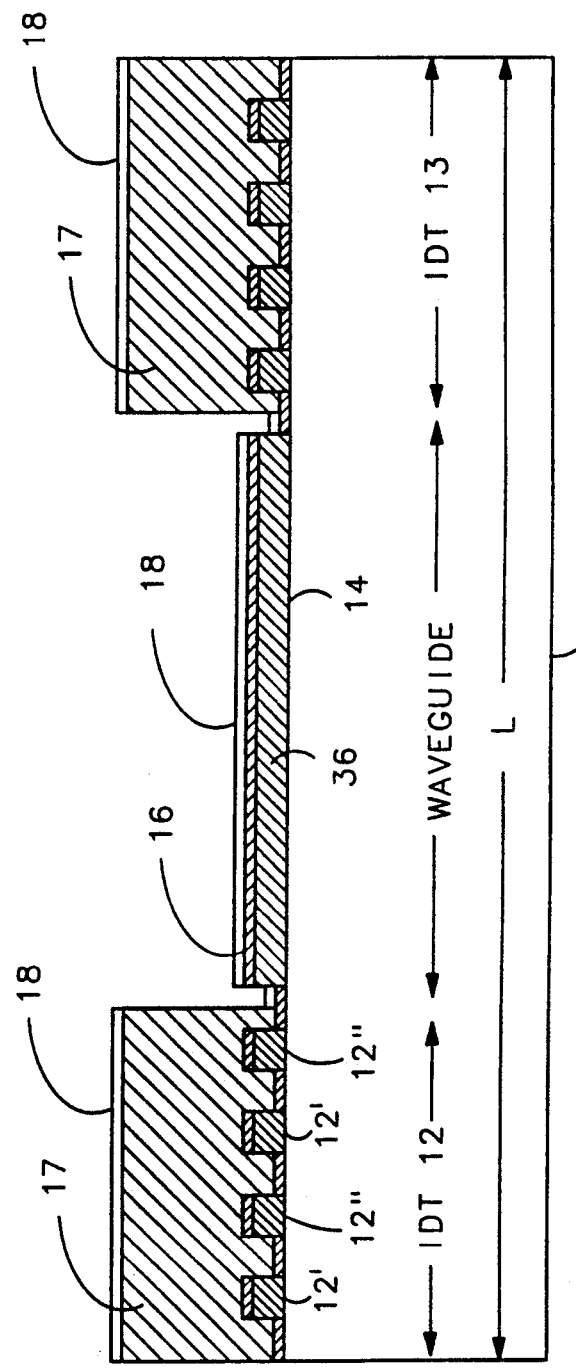
FIG. 3 is a side view of a STW sensor of the same type as in FIG. 1, except that it is mass loaded with a Love plate instead of a metal grating.

A top view of transducer 12 is shown in FIG. 2, illustrating the relationship between electrodes 12' and 12". An applied voltage difference between electrodes 12' and 12" produces between these electrodes an electric field that interacts electromechanically with the piezoelectric substrate. On top of surface 14, between IDTs 12 and 13 is formed a grating 15 having element width $W_2$ and spacing $S_2$ comparable to the width and spacing of IDTs 12 and 13. In many embodiments, this grating will be metallic, but it can also be dielectric. This grating functions as a surface trapping structure that traps the transverse acoustic wave at the surface of the substrate. In those embodiments in which the grating is metallic, the fingers of the grating can be shorted together with buss-bars to minimize the dielectric effects of the liquid on the performance of the sensor. FIG. 3 illustrates an alternate embodiment in which grating 15 (of FIG. 1) is replaced by a Love plate 36.

An attachment layer 16 can be deposited (e.g., by sputtering or evaporation) on top of elements 12, 13 and 14. Layer 16 should bind strongly and be hermetic to protect elements 11-15 from attack by chemicals. This layer has a thickness $T_2$ on the order of 10-1,000 Angstroms. For embodiments that are to serve as a chemical sensor, layer 16 is selected to provide a good chemically reactive surface for a chemically selective chemically reactive layer 18 to be deposited over grating 15. Silicon dioxide ($SiO_2$) is a good choice because there exists a large amount of literature on binding various chemically selective compounds to $SiO_2$. Layer 18 typically has a thickness $T_4$ on the order of a monolayer (for an antibody chemically reactive layer) to several microns.

In this embodiment, a thick shielding layer 17 is deposited over IDTs 12 and 13. This shielding layer serves a dual purpose. First, it should form a hermetic seal over the IDTs to protect them from corrosion. Second, it should prevent substantial shorting of the electrodes of the IDTs. When used as a chemical sensor in any water-based solution, IDTs will be exposed to the influence of such water solvent. Since water has a relatively high dielectric constant (on the order of 75), it can capacitively short out the electrodes of the IDTs. To prevent this, layer 17 must be thick enough (i.e., have a thickness $T_3$ on the order of or larger than the electrode spacing $S_1$ in the IDT) to prevent the water from substantially drawing the electric fields from the IDT electrodes out of substrate 11. For fabrication ease, layer 17 should also be easily patterned lithographically. One possible choice for layer 17 is silicone rubber. In other embodiments, this shielding layer can be omitted, for example in embodiments in which the immersion of the sensor into the liquid to be tested is not complete immersion. In such cases, the liquid need not come into contact with the transducers. Gaskets can also be included to encircle the transducers and provide for each transducer a lateral wall that keeps this liquid away from such transducer.

Figure 9A:
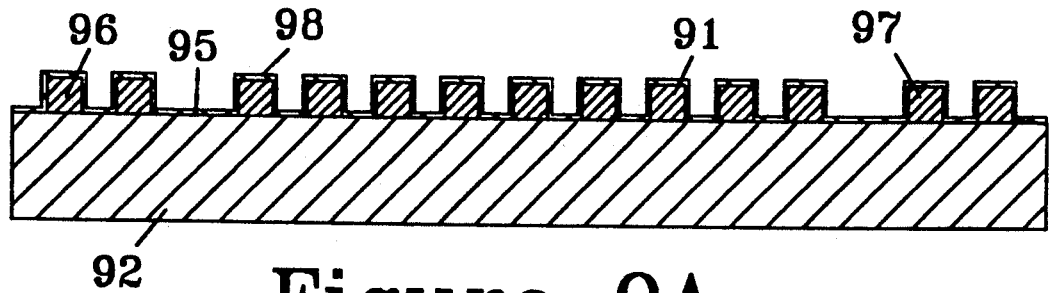
FIGS. 9A-9H illustrate different types of surface trapping structures that could be used to trap acoustic waves at a top surface of an STW device.
Figure 9B:
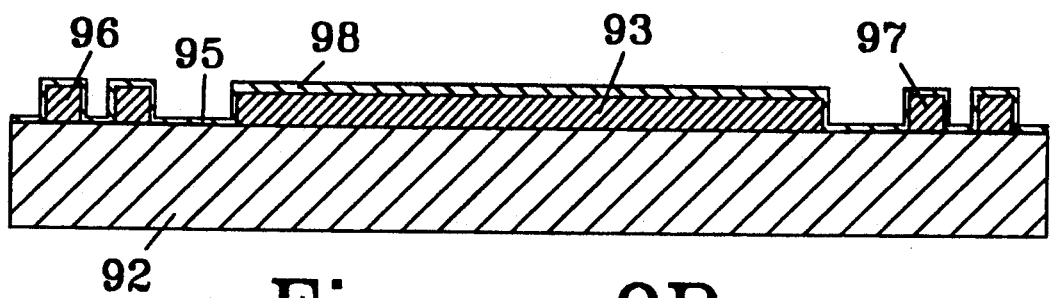

FIGS. 9A-9H illustrate several alternate embodiments of the surface trapping structure. FIGS. 9A and 9B, respectively, illustrate the use of a metal grating 91 and a metal plate 93 as the surface trapping structure attached to a sensing surface 95 of this sensor. Because metals are particularly dense, such gratings can be thinner than functionally comparable gratings of other materials. In addition, such metallic surface trapping structures can short out the piezoelectric crystal at its top surface, thereby lessening the stiffness of the substrate 92 at this top surface. This provides increased trapping of surface transverse waves at the top surface of the STW device. However, other materials can be used for the surface trapping structure and can exhibit other advantages. In this embodiment, an input transducer 96 launches acoustic waves toward an output transducer 97 and a chemically reactive layer 98 reacts with an associated class of solutes that are to be measured.

Figure 9C:
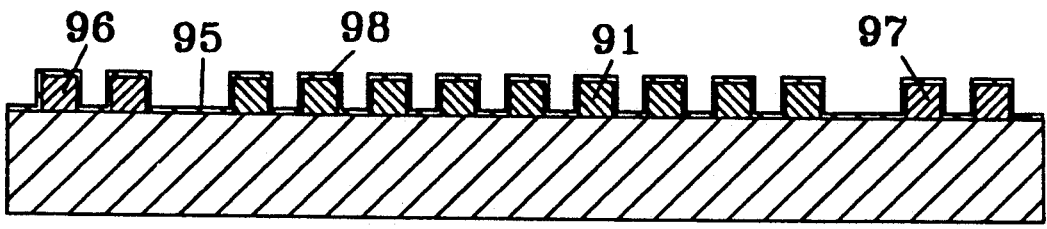
Figure 9D:
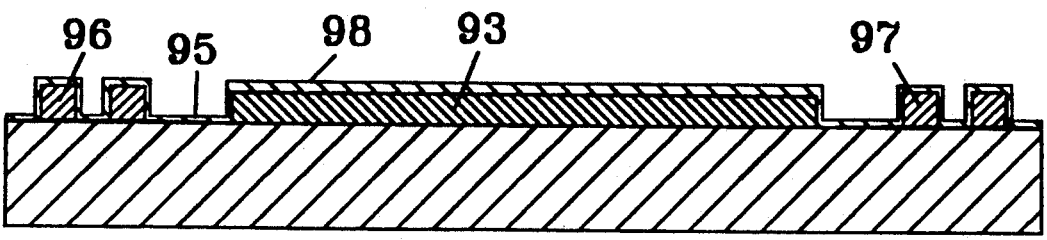
Figure 9E:
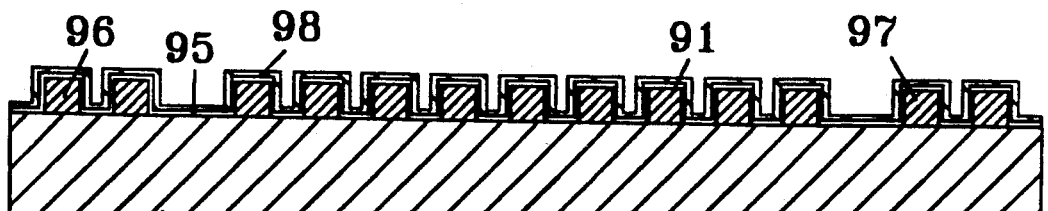
Figure 9F:
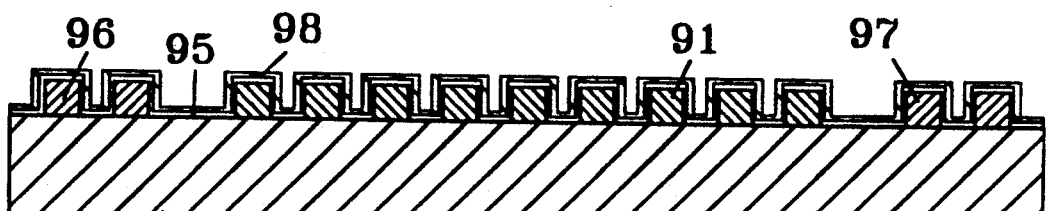
Figure 9G:
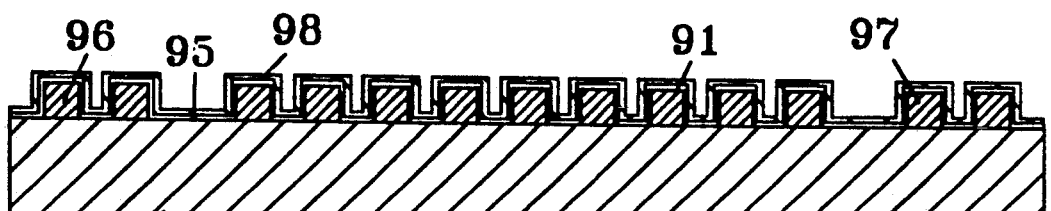
Figure 9H:
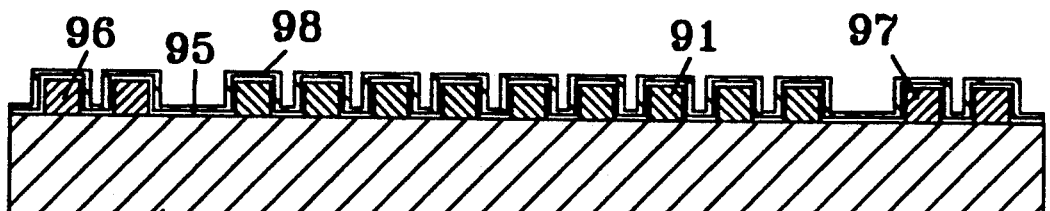

FIGS. 9C and 9D, respectively, illustrate the use of a dielectric grating and a dielectric plate. Such surface trapping structures are not subject to corrosion, as are metallic surface trapping structures when this mass sensor is completely immersed into corrosive chemicals. The particular dielectric chosen will often depend on the particular application for the mass sensor. For example, silicon dioxide is a particularly useful choice for a variety of reasons. It is a commonly utilized layer in integrated circuit processing. Therefore, its chemical and physical properties are well known and manufacturers have extensive experience and equipment applicable to producing such a layer. More significantly, silicon dioxide is widely utilized for capillaries in liquid chromatography so that there is an extensive base of knowledge related to the bonding of various attachment layers to silicon dioxide. In an embodiment in which the surface trapping structure is composed of silicon dioxide, no additional attachment layer 16 is required because the silicon dioxide surface trapping structure can perform this function.

The attachment layer 16 and the chemically reactive layer 18 are actually part of the surface trapping structure. Thus, as illustrated schematically in FIGS. 9E-9F, the surface trapping structure can include both a grating component and a plate component. The grating can be formed on top of the plate: by first forming a plate and then forming the grating on top of this plate; or by forming a plate and then etching the grating into the top portion of this plate. In other embodiments, the grating is first formed and then a covering layer (the plate portion of the combination plate/grating trapping structure) is formed over the grating. This latter embodiment has the advantage that the plate portion can be selected to be a material that protects the underlying grating portion (e.g., from corrosion or abrasion) and/or provides other advantageous surface properties, such as functioning as the attachment layer 16 and/or chemically reactive layer 18. FIGS. 9E-9H, respectively, illustrate the following cases: a metal plate on a metal grating; a dielectric plate on a dielectric grating; a dielectric plate on a metal grating; and a metal plate on a dielectric grating.

The particular choice of chemically reactive layer 18 will depend on the class of chemicals that are to be detected by this chemical sensor. In general, it should bind strongly to attachment layer 16 and must react selectively with the class of chemicals to be detected. Many such chemicals are known from the fields of gas and liquid chromatography. For example, the gas chromatography (GC) and liquid chromatography (LC) stationary phases are selective for a class of chemicals, but are not specific for a single chemical. In addition, when chemically reactive layer 18 is an antibody, it will be highly chemically specific to the antigen that binds to that antibody. In response to an antigen, the immune system of an animal generates an assortment of antibody molecules (each referred to as a monoclonal antibody) to different parts of an antigen, each molecule derived from a single clone of antibody producing cells. This mixture of monoclonal antibodies is referred to as polyclonal antibodies. Chemically reactive layer 18 can thus be either a monoclonal antibody or a polyclonal antibody. Typically, the bond formed between chemically reactive layer 18 and the chemical for which it is selective will be noncovalent. In biological applications, these noncovalent bonds are usually ionic bonds, hydrogen bonds and van der Waals bonds.

Chemically reactive layer 18 should also form a stiff linkage between attachment layer 16 and the chemical to be detected. As the stiffness of this linkage decreases, the effect of mass loading on the acoustic wave propagation velocity decreases, thereby also decreasing the sensitivity of the sensor. Thus, the required minimum stiffness of this linkage is determined by the desired device sensitivity and the sensitivity of associated electronics that detects a frequency shift or phase delay generated by this mass loading.

This STW sensor can be used with nucleic acid probes. In this application, the chemically reactive layer consists of identical molecules that are each a fragment of one strand of a nucleic acid. In a nucleic acid, each of these strands is covalently bonded to a complementary strand fragment. Therefore, this sensor detects the concentration of this complementary strand fragment in the liquid under test.

If this sensor is to be reusable, the bond between layer 18 and the chemicals to be detected must be reversible by convenient chemical means. In throw-away type sensors, this limitation is not required. In other embodiments discussed below, only the portion of the sensor containing the sensing surface is disposable.

Because the motion of top surface 14 is substantially parallel to this top surface, coupling of this motion into compressional modes in a liquid sample is extremely small. This coupling is so small that it is practical to use this sensor to measure the viscosity of the liquid sample. For a viscosity sensor, layer 16 is used to protect the sensor and layer 18 is not required (since the sensor is not specific in this mode of operation). In this application, the excess insertion loss due to the shear viscosity of the liquid on the phase shift or frequency can be measured to determine the viscosity.

Figure 5:
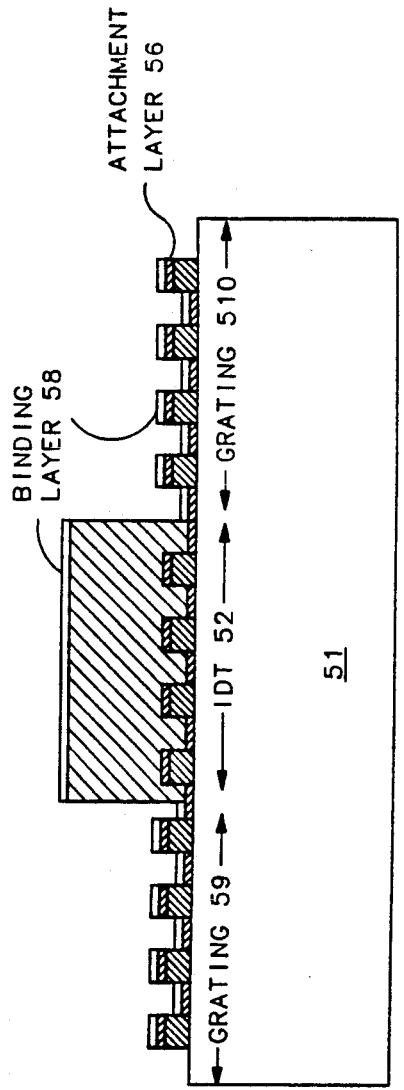
FIG. 5 is a side cross section of a surface transverse wave 1-port resonator sensor that is suitable for use as a viscosity sensor and/or a chemical sensor.

An alternate 1-port resonator embodiment is shown in FIG. 5. In this embodiment, a single IDT 52 is contained between a pair of gratings 59 and 510. Attachment layer 56 and chemically reactive layer 58 enable selective reaction with a particular solute or class of solutes in the solution under test. These two gratings serve a dual function. They reflect acoustic waves in this device, thereby defining the dimensions of a resonator cavity between these gratings. In addition, they trap the STW wave at the surface so that mass loading of these gratings by the solute that selectively reacts with chemically reactive layer 58 affects the velocity of the acoustic wave at the top surface of substrate 51, thereby enabling detection of the concentration of this solute by measuring the change in resonant frequency of the device when immersed in the solution under test. In addition to the particular STW embodiments presented herein, there are other well known embodiments of STW devices that can be used as these chemical sensors.

Figure 6:
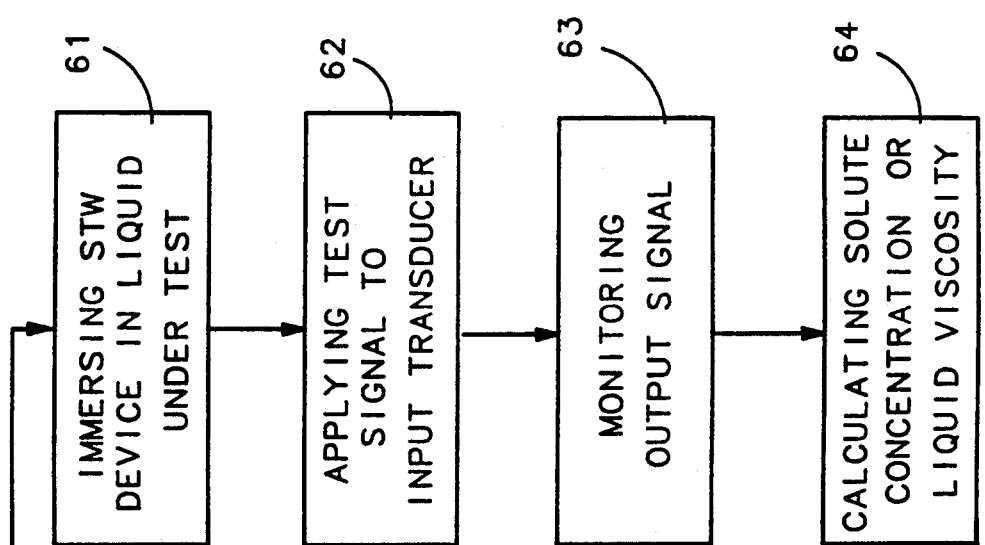
FIG. 6 illustrates the method of measuring a liquids viscosity and/or solute concentration by immersion of an STW device in the liquid.

In FIG. 6 are illustrated the method steps involved in measuring the viscosity or chemical concentration of a liquid. When measuring solute concentration, an STW device, having an attachment layer that bonds selectively to the solute, is immersed (step 61) in the liquid under test. Test signals are applied to an input of the STW device (step 62) and output signals from the STW device are monitored (step 63) for use in calculating the solute concentration (step 64). This STW device can have a chemically reactive layer, but if only viscosity is to be measured, such chemically reactive layer is typically not included.

Figure 7A:
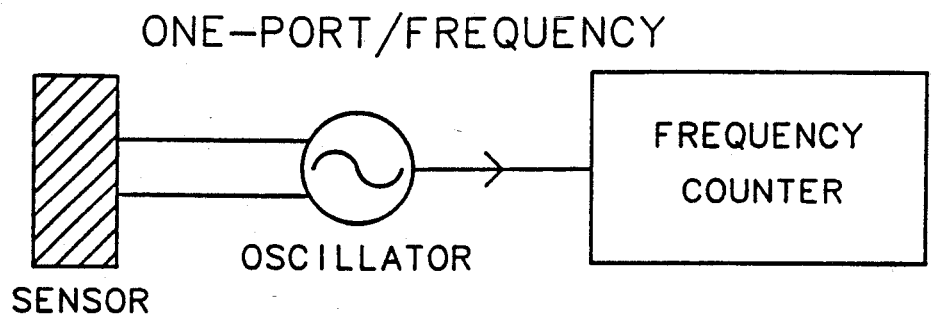
FIGS. 7A-7C illustrate three representative embodiments for converting propagation velocity variation in an STW device to either frequency or phase variation.
Figure 7B:
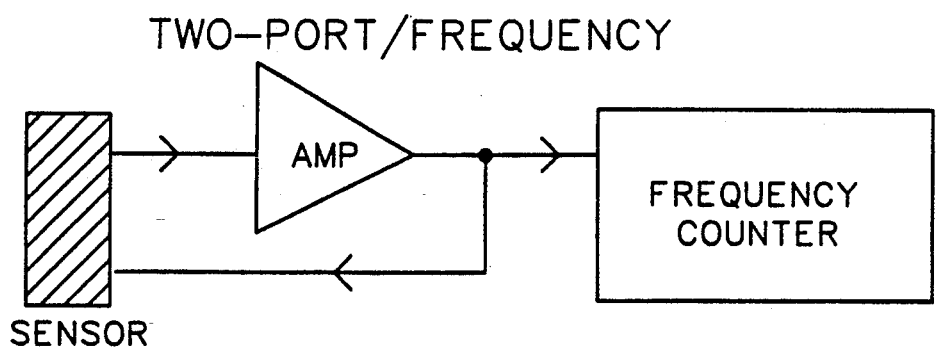

FIGS. 7A and 7B illustrate a pair of embodiments in which the frequency of the output signal indicates the solute concentration in the liquid of the solute that is selectively detected by this STW device. In FIG. 7A, an oscillator 71 is coupled to a one-port STW device 72 that adjusts the frequency of the oscillator. A frequency counter 73, coupled to the oscillator, measures the frequency of the oscillator. In FIG. 7B, a two-port STW device 74 is coupled in a feedback loop with an amplifier 75 and a frequency counter 76 measures the frequency of the signal at the output port of the amplifier.

Figure 7C:
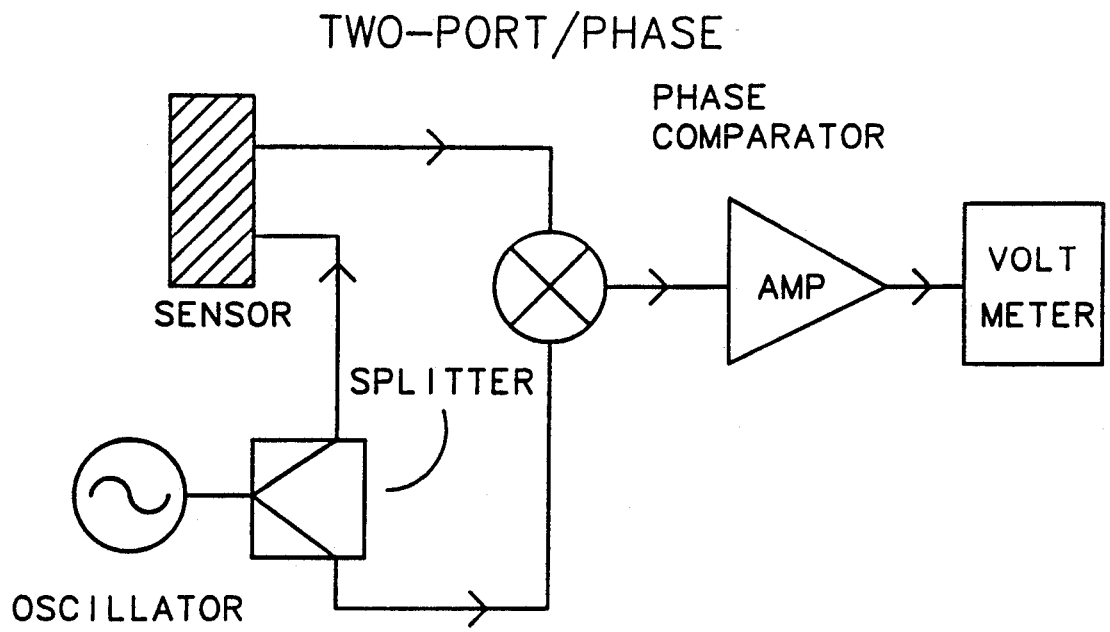

FIG. 7C illustrates a third embodiment in which the phase of the output signal indicates this concentration. In FIG. 7C, an oscillator 77 is connected to an input of a splitter 78. One output of this splitter is connected through a two-port STW device 79. The signals on the other output of this splitter and on an output of the STW device are combined at a mixer 712 to produce a signal that is applied to an input of an amplifier 710. An output signal from this amplifier is measured by a voltmeter 711 to produce a measure of the phase difference between the signals on the second output of the splitter and the output of the STW device. When the chemical concentration of a class of solutes in the solution is to be determined, in step 61, an STW device having a chemically reactive layer 18 that is chemically selective for a class of chemicals to be detected. When the chemical concentration of a particular solute in the solution is to be determined, in step 61, an STW device, having a chemically reactive layer 18 that is chemically specific to the solute to be detected, is used.

Figure 8:
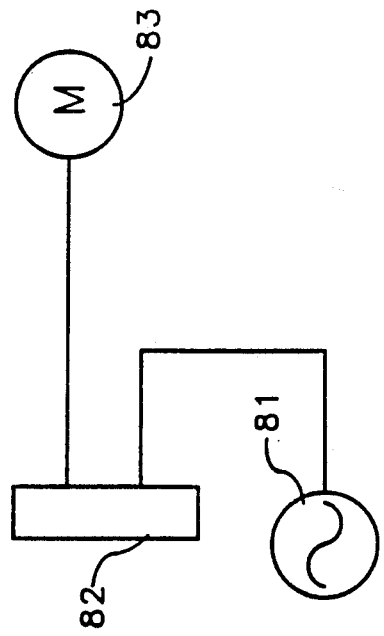
FIG. 8 illustrates an embodiment for measuring liquid viscosity with an STW device.

FIG. 8 illustrates an embodiment suitable for detecting the viscosity of a liquid. The liquid viscosity acts to damp a surface acoustic wave in the STW device. Therefore, the device in FIG. 8 includes a signal source 81 that provides a signal of a known amplitude. This signal is applied to a STW device 82 and the amplitude of an output signal is measured by a meter 83. As is illustrated in FIG. 6, additional steps 61'-63' can be included in the method of measurement to enable subtraction of a reference value of the output signal before calculation in step 64 of the solute concentration or the liquid viscosity. This is particularly useful for viscosity measurements because the small output signal value can contain a baseline correction that is a nonnegligible fraction of the output signal. In steps 61'-63', the STW device is immersed in a reference fluid, such as air, a test signal is applied to the input transducer of the STW device and the STW output signal is monitored. These two measured output signal amplitudes are then used in step 64 to calculate the viscosity of the liquid under test.

Figure 10A:
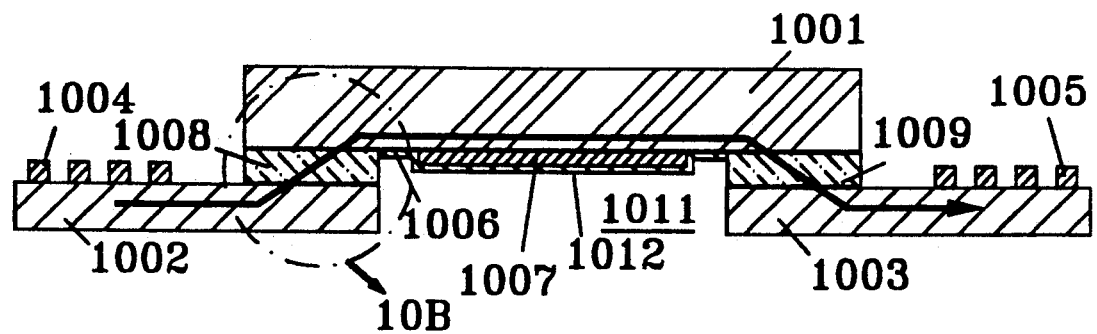
FIG. 10A illustrates a Love Wave mass sensor in which a nonpiezoelectric substrate is in contact with a pair of piezoelectric substrates that are used to launch an acoustic wave from the first of these piezoelectric substrates, through the nonpiezoelectric substrate, into the second of these piezoelectric substrates.

FIG. 10A illustrates, for the case of a Love Wave sensor, a mass sensor in which a nonpiezoelectric substrate 1001 is in contact with a pair of piezoelectric substrates 1002 and 1003 that are used to launch an acoustic wave in the first of these piezoelectric substrates, through the nonpiezoelectric substrate, into the second of these piezoelectric substrates. This acoustic wave is launched by a first transducer 1004 and is detected by a second transducer 1005. This acoustic wave is trapped at a sensing surface 1006 by a surface trapping structure, such as Love plate 1007. A chemically reactive layer 1012 reacts with an associated class of solutes that are to be detected by this sensor.

Figure 10B:
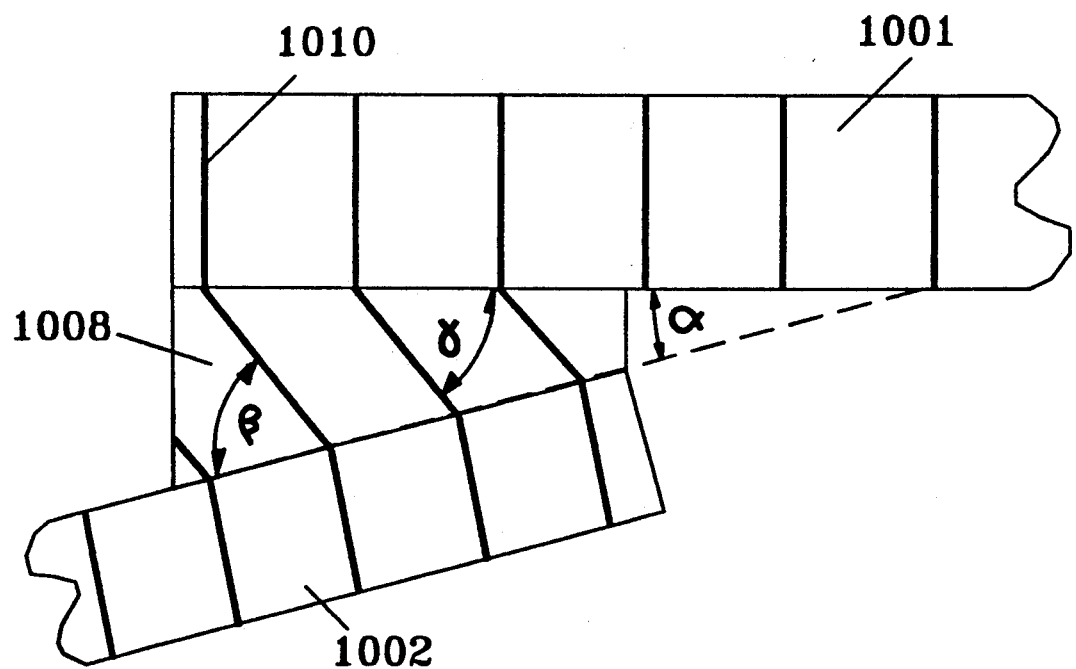
FIG. 10B illustrate the acoustic wave transfer wedge apex angle required to draw acoustic waves travelling in a first piezoelectric material, in a direction parallel to the sensing surface, into the nonpiezoelectric substrate in a direction parallel to the sensing surface.

An acoustic wave transfer wedge 1008 is attached between substrates 1001 and 1002 to draw the acoustic wave from substrate 1002 into substrate 1001. Similarly, an acoustic wave transfer wedge 1009 is attached between substrates 1001 and 1003 to draw the acoustic wave from substrate 1001 into substrate 1003. In general, the acoustic velocity $v_{1008}$ in transfer wedge 1008 and the acoustic velocity $v_{1009}$ in transfer wedge 1009 is less that the acoustic velocities $v_{1001}$, $v_{1002}$ and $v_{1003}$ in substrates 1001 and 1002 and 1003, respectively so that the acoustic wavefronts 1010 bend as illustrated in FIG. 10B. This figure illustrate the acoustic wave transfer wedge apex angle $\alpha$ required to draw acoustic waves travelling in a first piezoelectric material, in a direction parallel to the sensing surface, into the nonpiezoelectric substrate in a direction parallel to the sensing surface. The angles $\beta$ and $\gamma$ of wavefront bending satisfy the relationships $v_{1002} \cdot \sin \alpha = v_{1008} = v_{1001} \cdot \sin \gamma$. The vertex angle $\alpha$ of wedge 1008 is equal to $\beta$-$\gamma$ and is therefore nonzero if and only if the acoustic velocities in substrates 1001 and 1002 are unequal.

The embodiment of FIG. 10A provides two important advantages over the embodiments discussed above. First, transducers 1004 and 1005 are on the opposite side of this sensor from sensing surface 1006. Because of this, the liquid under test can be poured into cavity 1011 for measurement and thereby will not come into contact with transducer 1004 or transducer 1005. Therefore, no shielding layer is required for such a device. Second, for those applications in which the measured solvents are bound sufficiently strongly to the sensor that they cannot be economically removed, it is advantageous to have a sensor structure in which only an inexpensive part of the sensor need be replaced. It is therefore advantageous for the substrate containing the sensing surface to be an inexpensive material and for it to be detachable from the rest of the sensor so that it can be easily replaced with a clean substrate.

We claim:

1. A surface transverse wave device suitable for use as a sensor in a liquid, said device comprising:
    a piezoelectric substrate having a sensing surface;
    at least one transducer attached to said piezoelectric substrate for converting applied electric signals into acoustic signals in said piezoelectric substrate;
    a surface trapping structure, having dielectric material, for trapping acoustic waves in the substrate at the sensing surface of said substrate; and
    a chemically reactive layer that reacts with a class of solutes to be detected in said liquid.

2. A surface transverse wave device as in claim 1 wherein said surface trapping structure comprises a dielectric plate attached to said sensing surface.

3. A surface transverse wave device as in claim 1 wherein said surface trapping structure comprises a dielectric grating attached to said sensing surface.

4. A surface transverse wave device as in claim 3 wherein said surface trapping structure further comprises a plate that is attached to said sensing surface between said grating and said sensing surface.

5. A surface transverse wave device as in claim 1 wherein said surface trapping structure comprises:
   a metal plate attached to said sensing surface and having a top surface oriented away from said sensing surface; and
   a dielectric coating on the top surface of the metal plate.

6. A surface transverse wave device as in claim 1 wherein said surface trapping structure comprises:
   a metal grating attached to said sensing surface and having a top surface oriented away from said sensing surface; and
   a dielectric coating on the top surface of the metal grating.

7. A surface transverse wave device suitable for use as a sensor in a liquid, said device comprising:
   a piezoelectric substrate having a sensing surface;
   at least one transducer attached to said piezoelectric substrate for converting applied electric signals into acoustic signals in said piezoelectric substrate;
   a surface trapping structure, having dielectric material, for trapping acoustic waves in the substrate at the sensing surface of said substrate; and
   a chemically reactive layer that reacts with a class of solutes to be detected in said liquid;
   wherein said piezoelectric substrate has a composition and crystal cut such that said at least one transducer couples substantially only into shear horizontal acoustic waves, whereby this device exhibits a much greater sensitivity than a SAW device of comparable dimensions and arrangement of said at least one transducer.

8. A surface transverse wave device as in claim 7 wherein said piezoelectic substrate is a trigonal 32 type of crystal.

9. A surface transverse wave device as in claim 8 wherein said piezoelectric substrate is quartz.

10. A surface transverse wave device as in claim 9 wherein the cut of the substrate is a Y-rotated Z-cut.

11. A surface transverse wave device suitable for use as a sensor in liquids, said device comprising:
    a nonpiezoelectric substrate having a sensing surface;
    a surface trapping structure for trapping acoustic waves in the substrate at the sensing surface of said substrate;
    a chemically reactive layer that reacts with a class of solutes to be detected in said liquid; and
    means for converting an electrical signal into an acoustic signal that is trapped at the sensing surface of said nonpiezoelectric substrate.

12. A surface transverse wave device as in claim 11 wherein said means for converting comprises:
    a first piezoelectric substrate attached to said nonpiezoelectric substrate such that acoustic waves in this first piezoelectric substrate couple acoustic energy into acoustic waves in said nonpiezoelectric substrate; and
    a first transducer attached to said first piezoelectric substrate for converting applied electric signals into acoustic signals in said first piezoelectric substrate.

13. A surface transverse wave device as in claim 12 further comprising:
    an acoustic wave transfer wedge connected between the first piezoelectric substrate and said nonpiezoelectric substrate to transfer acoustic waves in said first piezoelectric substrate into said nonpiezoelectric substrate.

14. A surface transverse wave device as in claim 13 wherein said wedge has a vertex angle $\alpha$ selected such that a wave travelling in the first piezoelectric substrate parallel to said sensing surface crosses over into the piezoelectric substrate as a wave travelling parallel to the sensing surface.

15. A surface transverse wave device as in claim 12 wherein said piezoelectric substrate is attached to the sensing surface of the nonpiezoelectric substrate.

16. A surface transverse wave device as in claim 12 further comprising:
    a second piezoelectric substrate attached to said nonpiezoelectric substrate such that acoustic waves in the nonpiezoelectric substrate couple acoustic energy into acoustic waves in said second piezoelectric substrate; and
    a second transducer attached to said second piezoelectric substrate for converting acoustic signals in said second piezoelectric substrate into electrical signals.

17. A surface transverse wave device as in claim 12 wherein said first piezoelectric substrate is detachably attached to said nonpiezoelectric substrate, whereby said nonpiezoelectric substrate can be a disposable component of this device.

* * * * *